United States Patent

Hamley et al.

Patent Number: 6,083,952
Date of Patent: Jul. 4, 2000

[54] COMPOUNDS

[75] Inventors: Peter Hamley, Trussington; Austen Pimm; Alan Tinker, both of Loughborough, all of United Kingdom

[73] Assignee: Astra Pharmaceuticals Limited, Herts, United Kingdom

[21] Appl. No.: 09/125,174

[22] PCT Filed: Jun. 22, 1998

[86] PCT No.: PCT/SE98/01206

§ 371 Date: Aug. 11, 1998

§ 102(e) Date: Aug. 11, 1998

[87] PCT Pub. No.: WO99/01455

PCT Pub. Date: Jan. 14, 1999

[30] Foreign Application Priority Data

Jul. 1, 1997 [SE] Sweden ................................ 9702534

[51] Int. Cl.$^7$ .................................................. A01N 43/54
[52] U.S. Cl. ........................................... 514/257; 544/231
[58] Field of Search .............................. 544/231; 514/257

[56] References Cited

U.S. PATENT DOCUMENTS 5,883,102  3/1999  Hamley et al. ......................... 514/259

FOREIGN PATENT DOCUMENTS

97/14686  4/1997  WIPO.

OTHER PUBLICATIONS

Lochead et al, Abstract No. 1985:95488, "Use of chloroalkenylamines for the synthesis . . . ,", J. Chem. Soc., Perkin Trans. 1 (1984) (11) 2477–89.

Gesson et al, "α–N–Acyliminium IOn—2–Bromoalkene Cyclizations," Tetrahedron, vol. 49, No. 11, pp. 2239–2248 (1993).

*Primary Examiner*—Mukund J. Shah
*Assistant Examiner*—Tamthom N. Truong
*Attorney, Agent, or Firm*—Nixon & Vanderhye

[57] ABSTRACT

There are provided novel compounds of formula (I)

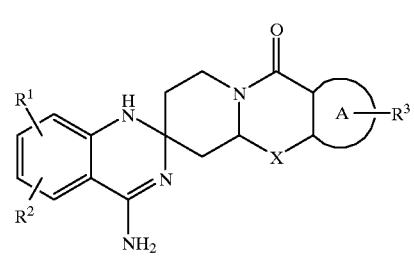

wherein A represents an aromatic carbocyclic ring or a 5- or 6-membered heterocyclic aromatic ring containing 1 to 3 heteroatoms which may be the same or different and are selected from O, N and S; X represents —$(CH_2)_n$— wherein n represents zero or 1; and $R^1$, $R^2$ and $R^3$ are as defined in the specification, and pharmaceutically acceptable salts thereof, and enantiomers and tautomers thereof; together with processes for their preparation, compositions containing them and their use in therapy. The compounds are inhibitors of nitric oxide synthase and are thereby particularly useful in the treatment or prophylaxis of inflammatory disease and pain.

14 Claims, No Drawings

COMPOUNDS

This application is a 371 of PCT/SE 98/01206, filed Jun. 22, 1998.

FIELD OF THE INVENTION

The present invention relates to novel compounds which are aminospiropiperidine quinazoline derivatives. The invention also concerns related aspects including processes for the preparation of the compounds, compositions containing them and their use as pharmaceuticals. There are also provided chemical intermediates useful for the production of the compounds.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been particularly implicated in the pathogenesis of inflammatory diseases. Regulation of these enzymes should therefore offer considerable potential in the treatment of a wide variety of disease states (J. E. Macdonald, Ann. Rep. Med. Chem., 1996, 31, 221–230).

WO 97/14686 discloses, amongst other compounds, aminospiropiperidine quinazoline derivatives of the following formula:

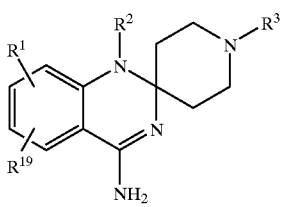

wherein $R^3$ represents various substituents, for use as pharmaceuticals. The treatment or prophylaxis of inflammatory conditions is disclosed as a particular pharmaceutical use.

DISCLOSURE OF THE INVENTION

According to the present invention, there is provided a compound of formula (I)

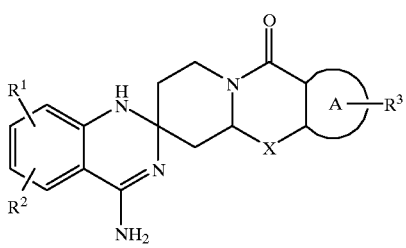

(I)

wherein:

$R^1$ and $R^2$ independently represent hydrogen, C1 to 6 alkyl, C2 to 6 alkenyl, C2 to 6 alkynyl, C1 to 6 alkoxy, C1 to 6 alkylthio, halogen, hydroxy, trifluoromethyl or amino;

$R^3$ represents one or more substituents independently selected from hydrogen, C1 to 6 alkyl, C2 to 6 alkenyl, C2 to 6 alkynyl, C1 to 6 alkoxy, C1 to 6 alkylthio, halogen, hydroxy, trifluoromethyl, amino, cyano, nitro, trifluoromethoxy, methanesulphonyl, sulphamoyl, —NR⁴R⁵, —COOR⁶, —CONR⁷R⁸, benzyloxy, phenyl, or a 5-membered heterocyclic aromatic ring containing 1 to 3 heteroatoms which may be the same or different and are selected from O, N and S, which phenyl or 5-membered heterocyclic aromatic ring is optionally substituted, the optional substituents being C1 to 6 alkyl, halogen, cyano, nitro, hydroxy, C1 to 6 alkoxy, trifluoromethyl and trifluoromethoxy;

$R^4$, $R^5$ and $R^6$ independently represent hydrogen or C1 to 6 alkyl;

$R^7$ and $R^8$ independently represent hydrogen, C1 to 6 alkyl or phenyl, which phenyl is optionally substituted by one or more groups independently selected from C1 to 6 alkyl, halogen, cyano, nitro, hydroxy, C1 to 6 alkoxy, trifluoromethyl and trifluoromethoxy;

X represents —$(CH_2)_n$—, wherein n represents zero or 1; and

A represents an aromatic carbocyclic ring or a 5- or 6-membered heterocyclic aromatic ring containing 1 to 3 heteroatoms which may be the same or different and are selected from O, N and S;

or a pharmaceutically acceptable salt, enantiomer, racemate or tautomer thereof.

The compounds of formula (I) and their pharmaceutically acceptable salts, enantiomers, racemates and tautomers have the advantage that they are potent inhibitors of the inducible isoform of the enzyme nitric oxide synthase (iNOS) present in macrophages.

The invention further provides a process for the preparation of such compounds or a pharmaceutically acceptable salt, enantiomer, racemate or tautomer thereof.

According to the invention there is also provided a compound of formula (I), or a pharmaceutically acceptable salt, enantiomer, racemate or tautomer thereof, for use as a medicament.

Another aspect of the invention provides the use of a compound of formula (I) or a pharmaceutically acceptable salt, enantiomer, racemate or tautomer thereof, in the manufacture of a medicament, for the treatment or prophylaxis of diseases or conditions in which inhibition of nitric oxide synthase activity is beneficial.

A more particular aspect of the invention provides the use of a compound of formula (I) or a pharmaceutically acceptable salt, enantiomer, racemate or tautomer thereof, in the manufacture of a medicament, for the treatment or prophylaxis of inflammatory disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt, enantiomer, racemate or tautomer thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt, enantiomer, racemate or tautomer thereof.

The compounds of the present invention may also be used advantageously in combination with a second pharmaceutically active substance, particularly in combination with a selective inhibitor of the inducible isoform of cyclooxygenase (COX-2). Thus, in a further aspect of the invention there is provided the use of a compound of formula (I) or a pharmaceutically acceptable salt, enantiomer, racemate or tautomer thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt, enantiomer, racemate or tautomer thereof in combination with a COX-2 inhibitor.

Preferably, A in formula (I) represents a benzo ring.

Preferably, $R^1$ in formula (I) represents hydrogen. Alternatively, it is preferred that $R^1$ in formula (I) represents fluoro.

Preferably, $R^2$ in formula (I) represents fluoro.

In another preferred embodiment, n in formula (I) has a value of zero.

Particular compounds of the invention include:

(R*R*)-4'-amino-5'-fluoro-1,3,4,10a-tetrahydrospiro[pyrido[2,1-a]isoindole-2,2'(1'H)quinazoline]-6-one;

(R*S*)-4'-amino-5'-fluoro-1,3,4,10a-tetrahydrospiro[pyrido[2,1-a]isoindole-2,2'(1'H)quinazoline]-6-one;

(R*R*)-4-amino-5-fluoro-3b',4',6',7'-tetrahydrospiro[quinazoline-2,5'(2H,9'H)-thieno[3,2-a]indolizine]-9'-one;

(R*S*)-4-amino-5-fluoro-3b',4',6',7'-tetrahydrospiro[quinazoline-2,5'(2H,9'H)-thieno[3,2-a]indolizine]-9'-one;

(R*R*)-4-amino-5-fluoro-6',7',9',9a'-tetrahydrospiro[quinazoline-2,8'(2H,4'H)-thieno[2,3-a]indolizine]-4'-one;

(R*S*)-4-amino-5-fluoro-6',7',9',9a'-tetrahydrospiro[quinazoline-2,8'(2H,4'H)-thieno[2,3-a]indolizine]-4'-one;

(R*R*)-4'-amino-7-chloro-5'-fluoro-1,3,4,10b-tetrahydrospiro[pyrido[2,1-a]isoindole-2,2'(1'H)-quinazoline]-6-one;

(R*S*)-4'-amino-7-chloro-5'-fluoro-1,3,4,10b-tetrahydrospiro[pyrido[2,1-a]isoindole-2,2'(1'H)-quinazoline]-6-one;

(R*R*)-4'-amino-8-chloro-5'-fluoro-1,3,4,10b-tetrahydrospiro[pyrido[2,1-a]isoindole-2,2'(1'H)-quinazoline]-6-one;

(R*S*)-4'-amino-8-chloro-5'-fluoro-1,3,4,10b-tetrahydrospiro[pyrido[2,1-a]isoindole-2,2'(1'H)-quinazoline]-6-one;

(R*R*)-4'-amino-9-chloro-5'-fluoro-1,3,4,10b-tetrahydrospiro[pyrido[2,1-a]isoindole-2,2'(1'H)-quinazoline]-6-one;

(R*S*)-4'-amino-9-chloro-5'-fluoro-1,3,4,10b-tetrahydrospiro[pyrido[2,1-a]isoindole-2,2'(1'H)-quinazoline]-6-one;

(R*R*)-4'-amino-10-chloro-5'-fluoro-1,3,4,10b-tetrahydrospiro[pyrido[2,1a]isoindole-2,2'(1'H)-quinazoline]-6-one;

(R*S*)-4'-amino-10-chloro-5'-fluoro-1,3,4,10b-tetrahydrospiro[pyrido[2,1-a]isoindole-2,2'(1'H)-quinazoline]-6-one;

(R*R*)-4'-amino-7,8-dichloro-5'-fluoro-1,3,4,10b-tetrahydrospiro[pyrido[2,1-a]isoindole-2,2'(1'H)-quinazoline]-6-one;

(R*S*)-4'-amino-7,8-dichloro-5'-fluoro-1,3,4,10b-tetrahydrospiro[pyrido[2,1-a]isoindole-2,2'(1'H)-quinazoline]-6-one;

(R*R*)-4'-amino-7-methyl-5'-fluoro-1,3,4,10b-tetrahydrospiro[pyrido[2,1-a]isoindole-2,2'(1'H)-quinazoline]-6-one;

(R*S*)-4'-amino-7-methyl-5'-fluoro-1,3,4,10b-tetrahydrospiro[pyrido[2,1-a]isoindole-2,2'(1'H)-quinazoline]-6-one;

(R*R*)-4'-amino-8-methyl-5'-fluoro-1,3,4,10b-tetrahydrospiro[pyrido[2,1-a]isoindole-2,2'(1'H)-quinazoline]-6-one;

(R*S*)-4'-amino-8-methyl-5'-fluoro-1,3,4,10b-tetrahydrospiro[pyrido[2,1-a]isoindole-2,2'(1'H)-quinazoline]-6-one;

(R*R*)-4'-amino-8-methoxy-5'-fluoro-1,3,4,10b-tetrahydrospiro[pyrido[2,1-a]isoindole-2,2'(1'H)-quinazoline]-6-one;

(R*S*)-4'-amino-8-methoxy-5'-fluoro-1,3,4,10b-tetrahydrospiro[pyrido[2,1-a]isoindole-2,2'(1'H)-quinazoline]-6-one;

(R*R*)-4'-amino-8-cyano-5'-fluoro-1,3,4,10b-tetrahydrospiro[pyrido[2,1-a]isoindole-2,2'(1'H)-quinazoline]-6-one;

(R*S*)-4'-amino-8-cyano-5'-fluoro-1,3,4,10b-tetrahydrospiro[pyrido[2,1-a]isoindole-2,2'(1'H)-quinazoline]-6-one;

(R*R*)-4'-amino-8-cyano-5',8'-difluoro-1,3,4,10b-tetrahydrospiro[pyrido[2,1-a]isoindole-2,2'(1'H)-quinazoline]-6-one;

(R*S*)-4'-amino-8-cyano-5',8'-difluoro-1,3,4,10b-tetrahydrospiro[pyrido[2,1-a]isoindole-2,2'(1'H)-quinazoline]-6-one;

(R*R*)-4'-amino-5'-fluoro-7,8,10,10a-tetrahydrospiro[pyrido[3,4-a]indolizine-9,2'(1'H)-quinazoline]-5-one;

(R*S*)-4'-amino-5'-fluoro-7,8,10,10a-tetrahydrospiro[pyrido[3,4-a]indolizine-9,2'(1'H)-quinazoline]-5-one;

(R*R*)-4'-amino-5'-fluoro-6b,7,9,10-tetrahydrospiro[naphtho[2,1-a]indolizine-8,2'(1'H)-quinazoline]-12-one;

(R*S*)-4'-amino-5'-fluoro-6b,7,9,10-tetrahydrospiro[naphtho[2,1-a]indolizine-8,2'(1'H)-quinazoline]-12-one;

and pharmaceutically acceptable salts, enantiomers, racemates or tautomers thereof.

Unless otherwise indicated, the term "C1 to 6 alkyl" referred to herein denotes a straight or branched chain alkyl group having from 1 to 6 carbon atoms or a cyclic alkyl group having from 3 to 6 carbon atoms. Examples of such groups include methyl, ethyl, n-propyl, i-propyl, n-butyl, i-butyl, t-butyl, cyclopentyl and cyclohexyl.

Unless otherwise indicated, the term "C2 to 6 alkenyl" referred to herein denotes a straight or branched chain alkyl group having from 2 to 6 carbon atoms and including one double bond or a cyclic alkyl group having from 3 to 6 carbon atoms and including one double bond. Examples of such groups include ethenyl, 1- and 2-propenyl, 2-methyl-2-propenyl, 2-butenyl, cyclopentenyl and cyclohexenyl.

Unless otherwise indicated, the term "C2 to 6 alkynyl" referred to herein denotes a straight or branched chain alkyl group having from 2 to 6 carbon atoms and including one triple bond. Examples of such groups include ethynyl, 1- and 2-propynyl and 2-butynyl.

Unless otherwise indicated, the term "C1 to 6 alkoxy" referred to herein denotes a straight or branched chain alkoxy group having from 1 to 6 carbon atoms. Examples of such groups include methoxy, ethoxy, n-propoxy, i-propoxy, n-butoxy, i-butoxy, s-butoxy and t-butoxy.

Other groups, for example, alkylthio, are to be interpreted similarly.

The process mentioned above, for the preparation of compounds of the invention, or a pharmaceutically acceptable salt, enantiomer, racemate or tautomer thereof comprises reaction of a compound of formula (II)

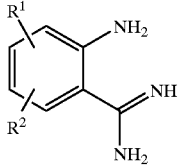
(II)

wherein $R^1$ and $R^2$ are as defined above, with a compound of formula (III) or a protected derivative thereof

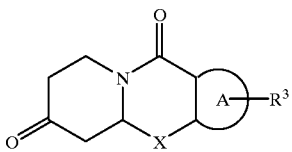
(III)

wherein $R^3$, A and X are as defined above.

The reaction may be carried out in a polar solvent, for example, methanol, ethanol, acetonitrile, dimethylformamide or dimethylsulphoxide at a suitable temperature, generally between 20° C. and the boiling point of the solvent, or without solvent at a temperature generally between 20° C. and 200° C. We have found that it is sometimes convenient to use the compounds of formula (III) in a protected form, for example as an acetal such as the diethoxy acetal. The process is then preferably carried out in the presence of an acid catalyst. The required acetals may be formed by reacting an unprotected compound of formula (III) with an alcohol such as ethanol using methods that are well known in the art.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer, racemate or tautomer thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Novel intermediates of formulae (II) and (III) form another aspect of the invention.

Compounds of formula (II) may be prepared using methods such as those described in WO 97/14686.

The preparation of compounds of formula (III) is either known per se or may be achieved using methods well known in the art. For example, compounds of formula (III) may be obtained by cyclisation of a compound of formula (IV)

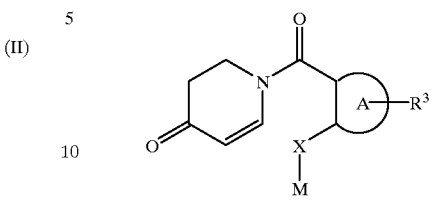
(IV)

wherein $R^3$, A and X are as defined above and M is an alkali or alkali earth metal.

Examples of such metals M include lithium, sodium, potassium or magnesium.

Compounds of formula (IV) may be formed in situ by treatment of a compound of formula

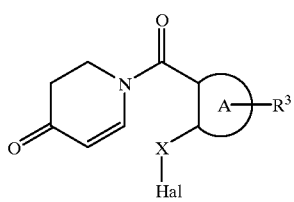
(IV')

wherein Hal represents a halogen atom, particularly bromine or iodine, with the metal M or an organometallic derivative or salt thereof, using procedures well known to the art. The reactions are best carried out in an aprotic solvent such as ether, tetrahydrofuran or diglyme at temperatures between −100° C. and 30° C.

Compounds of formula (IV') may be prepared by reaction of the compound of formula (V)

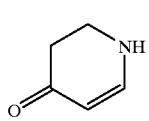
(V)

with an acid derivative of formula (VI)

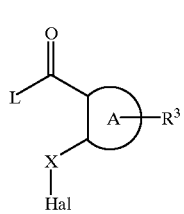
(VI)

wherein $R^3$, A, X and Hal are as defined above, and L is a leaving group. The reaction may be performed in an organic solvent, for example ethanol, dichloromethane or dimethylformamide at a temperature between 0° C. and the boiling point of the solvent. The reaction may be catalysed by the addition of a base; bases that may be used include organic amines (for example, triethylamine or pyridine) and alkali metal hydroxides, alkoxides or hydrides. Suitable leaving groups include halogen (especially chlorine) and imidazole. These acid derivatives may be prepared from the corresponding acid (compounds of formula (VI) wherein L is OH) using methods well known in the art.

Intermediate compounds may be used in protected form. Protecting groups and details of processes for their removal may be found by reference to the standard text "Protecting groups in Organic Synthesis", 2nd Edition (1991) by Greene and Wuts.

The compounds of the invention and intermediates thereto may be isolated from their reaction mixtures and, if necessary further purified, by using standard techniques.

The compounds of formula I may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (I) may exist in alternative tautomeric forms. Compounds of formula (I) are provided in another tautomeric form or as a mixture thereof.

The compounds of formula (I), and their pharmaceutically acceptable salts, enantiomers, racemates and tautomers, are useful because they possess pharmacological activity in animals. In particular, the compounds are active as inhibitors of the enzyme nitric oxide synthase. More particularly, they are inhibitors of the inducible isoform of the enzyme nitric oxide synthase present in macrophages and as such are predicted to be useful in therapy, for example, as anti-inflammatory agents.

The compounds and their pharmaceutically acceptable salts, enantiomers, racemates and tautomers are indicated for use in the treatment or prophylaxis of diseases or conditions in which synthesis or oversynthesis of nitric oxide synthase forms a contributory part. In particular, the compounds are indicated for use in the treatment of inflammatory conditions in mammals including man.

Conditions that may be specifically mentioned are:
osteoarthritis, rheumatoid arthritis, rheumatoid spondylitis, gouty arthritis and other arthritic conditions, inflamed joints;
eczema, psoriasis, dermatitis or other inflammatory skin conditions such as sunburn;
inflammatory eye conditions including uveitis and conjunctivitis;
lung disorders in which inflammation is involved, for example, asthma, bronchitis, pigeon fancier's disease, farmer's lung, acute respiratory distress syndrome;
bacteraemia, endotoxaemia (septic shock), aphthous ulcers, gingivitis, pyresis, pain and pancreatitis;
conditions of the gastrointestinal tract including Crohn's disease, atrophic gastritis, gastritis varialoforme, ulcerative colitis, coeliac disease, regional ileitis, peptic ulceration, irritable bowel syndrome, damage to the gastrointestinal tract resulting from infections by, for example, *Helicobacter pylori*, or from treatments with non-steroidal anti-inflammatory drugs;
and other conditions associated with inflammation.

The compounds will also be useful in the treatment and alleviation of acute or persistent inflammatory or neuropathic pain or pain of a central origin.

The compounds of formula (I) and their pharmaceutically acceptable salts, enantiomers, racemates and tautomers may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the treatment of vascular complications associated with diabetes and in cotherapy with cytokines, for example TNF or interleukins.

The compounds of formula (I) may also show inhibitory activity against the neuronal isoform of nitric oxide synthase. Thus they may also be useful in the treatment of hypoxia, for example in cases of cardiac arrest and stroke, neurodegenerative disorders including nerve degeneration and/or nerve necrosis in disorders such as hypoxia, hypoglycemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Korsakoff's disease, imbecility relating to a cerebral vessel disorder, sleeping disorders, schizophrenia, depression, autism, seasonal affective disorder, jet-lag, depression or other symptoms associated with Premenstrual Syndrome (PMS), anxiety and septic shock. Compounds of formula (I) may also be expected to show activity in the prevention and reversal of tolerance to opiates and diazepines, treatment of drug addiction, treatment of migraine and other vascular headaches, neurogenic inflammation, in the treatment of gastrointestinal motility disorders, cancer and in the induction of labour.

For the above mentioned therapeutic indications, the dosage administered will, of course, vary with the compound employed, the mode of administration and the treatment desired.

However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt, enantiomer, racemate or tautomer thereof.

There is also provided a process for the preparation of such a pharmaceutical composition which comprises mixing the ingredients.

The compounds of formula (I), and pharmaceutically acceptable derivatives thereof, may also be advantageously used in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

Preparation 1
2,3-Dichloro-6-iodobenzoic acid chloride
a) 2,3-Dichloro-6-iodobenzoic acid n-Butyllithium (1.45M solution in hexane, 19.4 mmol, 13.4 ml) was added dropwise to a stirred solution of diisopropylamine (21.4 mmol, 3.0 ml) in THF (90 ml) at 0° C. After 30 minutes, the solution was cooled to −78° C. and a solution of 1,2-dichloro-4-iodobenzene (5.30 g, 19.4 mmol) in THF (10 ml) was added dropwise. After 10 minutes, solid carbon dioxide was added cautiously and the mixture allowed to warm to room temperature over 16 h. The mixture was diluted with water and extracted twice with ethyl acetate. The aqueous layer was acidified with dilute aqueous hydrochloric acid and then extracted twice with ethyl acetate. The extracts were dried over sodium sulphate and evaporated to give the title compound as a yellow solid (3.59 g). 300 MHz $^1$H NMR (d$_6$-DMSO) 11.5 (1H, br.s), 7.82 (1H, d, J 8.4 Hz), 7.44 (1H, d, J 8.4 Hz).

b) 2,3-Dichloro-6-iodobenzoic acid chloride

DMF (one drop) was added to a stirred solution of 2,3-dichloro-6-iodobenzoic acid (1.53 g, 4.83 mmol) and oxalyl chloride (2 ml) in ethyl acetate (20 ml). After 2 hours, the solution was evaporated and the product was used immediately.

Preparation 2
3-Cyano-6-iodobenzoic acid chloride
a) 2-Amino-5-cyanobenzoic acid methyl ester 2-Amino-5-bromobenzoic acid methyl ester (4.6 g, 20 mmol) and copper (I) cyanide (3.6 g, 40 mmol) were heated at 200° C. in N-methylpyrrolidinone (20 ml) for 4 h. After cooling to room temperature, the solution was diluted with water, extracted with ethyl acetate, the aqueous extract acidified with 2N hydrochloric acid and filtered. The organic layer was separated, dried over magnesium sulphate and evaporated. The residue was purified by flash column chromatography on silica eluting with 50% ethyl acetate in hexane to yield the title compound as a colourless oil (1.0 g). MS (+EI) $^m$/z 176 [M$^+$].

b) 2-Iodo-5-cyanobenzoic acid methyl ester

Sodium nitrite (0.8 g, 11.4 mmol) in water (10 ml) was added dropwise over 10 minutes to a stirred solution of 2-amino-5-cyanobenzoic acid methyl ester (2.0 g, 11.4 mmol) in water (30 ml) and conc. sulphuric acid (15 ml) at 0° C. After a further 15 minutes at 5° C., a solution of potassium iodide (3.5 g, 21 mmol) in water (30 ml) was quickly added and the mixture allowed to warm to room temperature. 10% Aqueous sodium thiosulphate was added, the mixture extracted with ethyl acetate, the extract dried over magnesium sulphate and evaporated. The residue was purified by flash column chromatography on silica eluting with 20% ethyl acetate in hexane to yield the title compound as a colourless oil (2.8 g). MS (+EI) $^m$/z 287 [M$^+$].

c) 2-Iodo-5-cyanobenzoic acid

A solution of sodium hydroxide (0.44 g, 11 mmol) in water (10 ml) was added to 2-iodo-5-cyanobenzoic acid methyl ester (2.7 g, 9.4 mmol) in methanol. The mixture was stirred for 20 h, then most of the solvent was evaporated and the residue acidified with 2N hydrochloric acid. The resulting precipitate was filtered off and dried to give a white solid (1.7 g). MS (−CI) $^m$/z 272 [M−H]$^+$.

d) 2-Iodo-5-cyanobenzoic acid chloride

This was prepared by the method of Preparation 1(b) and was used directly.

Other acid chlorides are either known per se or were prepared from the known acids by the method of Preparation 1(b).

Preparation 3
1-(2-Bromo-6-chlorobenzoyl)-2,3-dihydro-4-pyridinone

A solution of 2-bromo-6-chlorobenzoic acid chloride (0.5 mmol) in dichloromethane (5 ml) was added dropwise to a solution of 2,3-dihydro-4-pyridinone (5.1 mmol, 495 mg) and triethylamine (1.2 ml) in dichloromethane (20 ml). After stirring for 30 minutes, the solution was diluted with water, separated, the aqueous extract further extracted with dichloromethane, the combined organic extracts combined and washed with brine, dried over sodium sulphate and evaporated. The residue was purified by flash column chromatography on silica eluting with 30% ethyl acetate in hexane to yield the title compound as a pale yellow oil (629 mg). MS (+CI) $^m$/z 316 [M+H]$^+$.

The following intermediates were similarly prepared from 2,3-dihydro-4-pyridinone and the appropriate acid chloride:

(i) 1-(2-Bromo-5-methylbenzoyl)-2,3-dihydro-4-pyridinone: colourless oil, MS (+EI) $^m$/z 293/295 [M$^+$].
(ii) 1-(3-Bromo-4-pyridinoyl)-2,3-dihydro-4-pyridinone: white solid, MS (+EI) $^m$/z 280/282 [M$^+$].
(iii) 1-(2,3-Dichloro-6-iodobenzoyl)-2,3-dihydro-4-pyridinone: white solid, MS (+EI) $^m$/z 395/397 [M$^+$].
(iv) 1-(5-Cyano-2-iodobenzoyl)-2,3-dihydro-4-pyridinone: colourless oil, used without purification.
(v) 1-(2-Methyl-6-iodobenzoyl)-2,3-dihydro-4-pyridinone: MS (+EI) $^m$/z 341 [M$^+$].
(vi) 1-(2-Bromo-3-chlorobenzoyl)-2,3-dihydro-4-pyridinone: MS (+EI) $^m$/z 313/315 [M$^+$].
(vii) 1-(2-Bromo-4-chlorobenzoyl)-2,3-dihydro-4-pyridinone: MS (+EI) $^m$/z 314 [M$^+$].
(viii) 1-(2-Bromo-5-chlorobenzoyl)-2,3-dihydro-4-pyridinone: MS (+EI) $^m$/z 314 [M$^+$].
(ix) 1-(2-Bromo-3-thienoyl)-2,3-dihydro-4-pyridinone: MS (−CI) $^m$/z 284/286 [M−H]$^+$.
(x) 1-(2-Bromo-5-methoxybenzoyl)-2,3-dihydro-4-pyridinone; MS (+EI) $^m$/z 309/311 [M$^+$].
(xi) 1-(2-Iodo-1-naphthoyl)-2,3-dihydro-4-pyridinone: MS (−CI) $^m$/z 376 [M−H]$^+$.
(xii) 1-(2-Iodo-3-thienoyl)-2,3-dihydro-4-pyridinone: colourless oil: 300 MHz $^1$H NMR (d$_6$-DMSO) 7.55 (1H, d, J 5.4 Hz), 7.47–7.43 (1H, m), 7.00 (1H, d, J 5.4 Hz), 5.40 (1H, d, J 8.1 Hz), 4.18 (2H, t, J 7.2 Hz), 2.68 (2H, t, J 7.2 Hz).

Preparation 4
(±)-7-Chloro-1,3,4,10b-tetrahydropyrido[2,1-a]isoindole-2,6-dione

A mixture of 1-(2-bromo-6-chlorobenzoyl)-2,3-dihydro-4-pyridinone (Preparation 3) (300 mg, 0.954 mmol), triethylamine (0.39 mmol, 0.54 ml), formic acid (0.05 ml, 1.3 mmol) and di(triphenylphosphine)diacetoxypalladium (47 mg, 0.063 mmol) in DMF (3 ml) was heated to 80° C. for 2 h. The cooled solution was filtered through celite, diluted with water, extracted twice with ethyl acetate, the extracts dried over sodium sulphate and evaporated. The residue was purified by flash column chromatography on silica eluting with 50% ethyl acetate in hexane to yield the title compound as a colourless oil (70 mg). MS (+CI) $^m$/z 235/237 [M+H]$^+$.

The compounds of Preparations 5 to 7 were synthesised using the method of Preparation 4:

Preparation 5
(±)-7,8-Dichloro-1,3,4,10b-tetrahydropyrido[2,1-a]isoindole-2,6-dione From 1-(2,3-dichloro-6-iodobenzoyl)-2,3-dihydro-4-pyridinone. White solid. MS (+EI) $^m$/z 269/271 [M$^+$].

Preparation 6
(±)-8-Chloro-1,3,4,10b-tetrahydropyrido[2,1-a]isoindole-2,6-dione From 1-(2-bromo-5-chlorobenzoyl)-2,3-dihydro-4-pyridinone. Colourless oil. MS (+EI) $^m/z$ 235/237 [M⁺].

Preparation 7
(±)-3b,4,6,7-tetrahydrothieno[3,2-a]indolizine-5,9-dione

From 1-(3-bromo-2-thienoyl)-2,3-dihydro-4-pyridinone. Colourless oil. MS (+CI) $^m/z$ 208 [M+H]⁺.

Preparation 8
(±)-8-Methyl-1,3,4,10b-tetrahydropyrido[2,1-a]isoindole-2,6-dione A mixture of 1-(2-bromo-5-methylbenzoyl)-2,3-dihydro-4-pyridinone (1.19 g, 4.03 mmol), tri-n-butyltin hydride (1.14 ml, 4.24 mmol) and azobis(isobutyronitrile) (AIBN, 66 mg, 10 mol %) in toluene (40 ml) was heated at 95° C. for 2 h, cooled, evaporated and purified by flash column chromatography on silica eluting with 30% ethyl acetate in hexane to yield the title compound as a pale yellow oil (276 mg), MS (+EI) $^m/z$ 215 [M⁺].

The compounds of Preparations 9 to 12 were prepared using the method of Preparation 8:

Preparation 9
(±)-8-Cyano-1,3,4,10b-tetrahydropyrido[2,1-a]isoindole-2,6-dione From 1-(5-cyano-2-iodobenzoyl)-2,3-dihydro-4-pyridinone. MS (−CI) $^m/z$ 226 [M⁺].

Preparation 10
(±)-7,8,10,10a-Tetrahydropyrido[3,4-a]indolizine-5,9-dione

From 1-(3-bromo-4-pyridinoyl)-2,3-dihydro-4-pyridinone. MS (+EI) $^m/z$ 202 [M⁺].

Preparation 11
(±)-7-Methyl-1,3,4,10b-tetrahydropyrido[2,1-a]isoindole-2,6-dione From 1-(2-Methyl-6-iodobenzoyl)-2,3-dihydro-4-pyridinone. MS (+EI) $^m/z$ 215 [M⁺].

Preparation 12
(±)-6b,7,9,10-tetrahydronaphtho[2,1-a]indolizine-8,12-dione

From 1-(2-iodo-1-naphthoyl)-2,3-dihydro-4-pyridinone. MS (+CI) $^m/z$ 252 [M+H]⁺.

Preparation 13
(±)-8-Methoxy-1,3,4,10b-tetrahydropyrido[2,1-a]isoindole-2,6-dione Butyl lithium (3.1 ml, 0.9 M in hexanes, 2.8 mmol) was added dropwise to a solution of 1-(2-bromo-5-methoxybenzoyl)-2,3-dihydro-4-pyridinone (0.75 g, 2.4 mmol) in THF (20 ml) at −78° C. After stirring for 2 h, the reaction was quenched with water, extracted with ethyl acetate, the extract dried over magnesium sulphate and evaporated. The residue was purified by flash column chromatography on silica eluting with 50% ethyl acetate in hexane to yield the title compound as a colourless oil (240 mg). MS (+EI) $^m/z$ 231 [M⁺].

The compounds of Preparations 14 to 16 were prepared using the method of Preparation 13:

Preparation 14
10-Chloro-1,3,4,10b-tetrahydropyrido[2,1-a]isoindole-2,6-dione From 1-(2-bromo-3-chlorobenzoyl)-2,3-dihydro-4-pyridinone: colourless oil. MS (+EI) $^m/z$ 235/237 [M⁺].

Preparation 15
9-Chloro-1,3,4,10b-tetrahydropyrido[2,1-a]isoindole-2,6-dione

From 1-(2-bromo-4-chlorobenzoyl)-2,3-dihydro-4-pyridinone: colourless oil. MS (+EI) $^m/z$ 235/237 [M⁺].

Preparation 16
6,7,9,9a-Tetrahydrothieno[2,3-a]indolizine-4,8-dione

From 1-(2-bromo-3-thienoyl)-2,3-dihydro-4-pyridinone. MS (+CI) $^m/z$ 208 [M+H]⁺.

EXAMPLE 1

(±)-(R*R*)-4'-Amino-5'-fluoro-1,3,4,10a-tetrahydrospiro[pyrido[2,1-a]isoindole-2,2'(1'H)quinazoline]-6-one A solution of 2-amino-6-fluorobenzamidine (0.13 g, 0.61 mmol) and 1,3,4,10a-tetrahydro[pyrido[2,1-a]]isoindole-2,6-dione (0.12 g, 0.59 mmol) (J.C.S. Perkin Trans. 1, 1984, 2477; Tetrahedron, 1993, 2239) in ethanol (15 ml) was stirred at reflux for 18 h. The mixture was cooled and filtered to give a yellow solid (0.1 g), which was purified by flash column chromatography on neutral alumina, eluting with dichloromethane/methanol (99:1 to 95:5) as eluent to afford a single diastereoisomer of the title compound (containing the RR and SS enantiomers), as a yellow solid (0.05 g). M.p. 207–209° C.

EXAMPLE 2

(±)-(R*S*)-4'-Amino-5'-fluoro-1,3,4,10a-tetrahydrospiro[pyrido[2,1-a]isoindole-2,2'(1'H)quinazoline]-6-one The filtrate obtained after the precipitation of the product of Example 1 was concentrated to give a brown oil (0.19 g). Purification by flash column chromatography on neutral alumina, eluting with dichloromethane/methanol (99:1 to 95:5) as eluent gave a second diastereoisomer of the title compound (containing the RS and SR enantiomers), as a yellow solid (0.03g). M.p. 184–186° C.

EXAMPLE 3
(±)-(R*R*)-4-Amino-5-fluoro-3b',4',6',7'-tetrahydrospiro[quinazoline-2,5'(2H,9'H)-thieno[3,2-a]indolizine]-9'-one

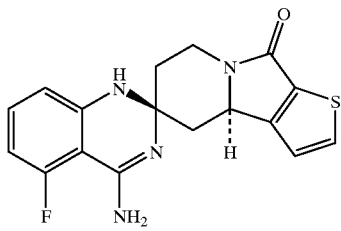

A solution of 2-amino-6-fluorobenzamidine dihydrochloride (100 mg., 44 mmol) and 3b,4,6,7-tetrahydrothieno[3,2-a]indolizine-5,9-dione (Preparation 7, 80 mg, 39 mmol) in ethanol (10 ml) was heated at reflux for 5 h. The solvent was evaporated and the residue separated by chromatography on silica using dichloromethane-methanol mixtures as eluent. The first eluted fraction provided the title compound (63 mg, 43%) as a pale yellow solid, m.p. 193–195° C. MS (+CI) $^m$/z 343 [M+H]$^+$.

EXAMPLE 4
(±)-(R*S*)-4-Amino-5-fluoro-3b',4',6',7'-tetrahydrospiro[quinazoline-2,5'(2H,9'H)-thieno[3,2-a]indolizine]-9'-one

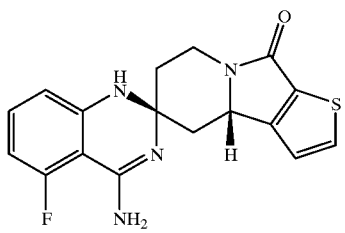

The second eluted fraction from the chromatography described in Example 3 afforded the title compound (33 mg, 22%), m.p. 218–220° C. MS (+CI) $^m$/z 343 [M+H]$^+$.

The compounds of Examples 5 to 30 were made by the method of Examples 3 and 4 using the intermediates stated.

The compounds of Examples 5 and 6 were obtained from 2-amino-6-fluorobenzamidine dihydrochloride and 6,7,9,9a-tetrahydrothieno[2,3-a]indolizine-4,8-dione (Preparation 16).

EXAMPLE 5
(±)-(R*R*)-4-Amino-5-fluoro-6',7',9',9a'-tetrahydrospiro[quinazoline-2,8'(2H,4'H)-thieno[2,3-a]indolizine]-4'-one

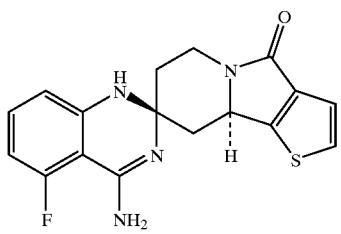

Obtained as the hydrochloride salt, m.p. >275° C. MS (+CI) $^m$/z 343 [M+H]$^+$.

EXAMPLE 6
(±)-(R*S*)-4-Amino-5-fluoro-6',7',9',9a'-tetrahydrospiro[quinazoline-2,8'(2H,4'H)-thieno[2,3-a]indolizine]-4'-one

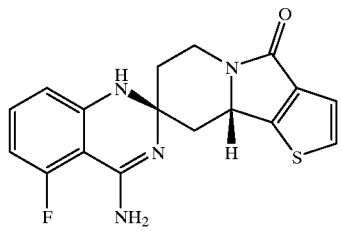

Obtained as the hydrochloride salt, m.p. 225–230° C. MS (+CI) $^m$/z 343 [M+H]$^+$.

The compounds of Examples 7 and 8 were obtained from 2-amino-6-fluorobenzamidine dihydrochloride and 7-chloro-1,3,4,10b-tetrahydropyrido[2,1-a]isoindole-2,6-dione (Preparation 4).

EXAMPLE 7
(±)-(R*R*)-4'-Amino-7-chloro-5'-fluoro-1,3,4,10b-tetrahydrospiro[pyrido[2,1-a]isoindole-2,2'(1'H)-quinazoline]-6-one hydrochloride

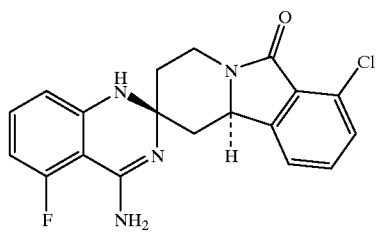

MS (+CI) $^m$/z 371/373 [M+H]$^+$; 300 MHz $^1$H NMR (d$_6$-DMSO) 7.62 (1H, d, J 7.5 Hz), 7.54 (1H, t, J 7.5 Hz), 7.45 (1H, d, J 7.2 Hz), 7.13 (1H, dt, J 6.6, 6.6, 8.1 Hz), 6.59 (1H, s), 6.40 (1H, d, J 7.2 Hz), 6.37–6.33 (1H, m), 5.85–5.8 (2H, br.s), 4.79 (1H, dd, J3.3, 11.4 Hz), 4.12 (1H, dd, J 3.9, 13.8 Hz), 3.40–3.35 (1H, m), 2.60–2.55 (1H, m), 1.91 (1H, d, J 12 Hz), 1.37 (1H, dt, J 5.7, 12.9,12.9 Hz), 1.04 (1H, t, J 11.7 Hz).

EXAMPLE 8
(±)-(R*S*)-4'-Amino-7-chloro-5'-fluoro-1,3,4,10b-tetrahydrospiro[pyrido[2,1-a]isoindole-2,2'(1'H)-quinazoline]-6-one hydrochloride

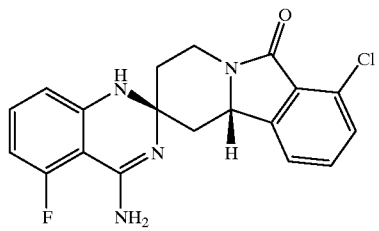

MS (+CI) $^m$/z 371/373 [M+H]$^+$; 300 MHz $^1$H NMR (d$_6$-DMSO) 7.61–7.46 (4H, m), 7.2–7.20 (2H, m), 6.74 (1H, d, J 8.1 Hz), 6.44 (1H, dd, J 8.4, 12.3 Hz), 4.75 (1H, dd, J 3.6, 3.9 Hz), 3.32–3.19 (1H, m), 2.0–1.95 (1H, m), 1.5–1.4 (1H, m), 1.3–1.1 (1H, m).

The compounds of Examples 9 and 10 were obtained from 2-amino-6-fluorobenzamidine dihydrochloride and 8-chloro-1,3,4,10b-tetrahydropyrido[2,1-a]isoindole-2,6-dione (Preparation 6).

EXAMPLE 9

(±)-(R*R*)-4'-Amino-8-chloro-5'-fluoro-1,3,4,10b-tetrahydrospiro[pyrido[2,1-a]isoindole-2,2'(1'H)-quinazoline]-6-one

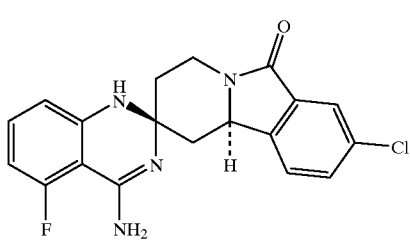

Obtained as the hydrochloride salt, m.p. 308° C. (dec.).

EXAMPLE 10

(±)-(R*S*)-4'-Amino-8-chloro-5'-fluoro-1,3,4,10b-tetrahydrospiro[pyrido[2,1-a]isoindole-2,2'(1'H)-quinazoline]-6-one

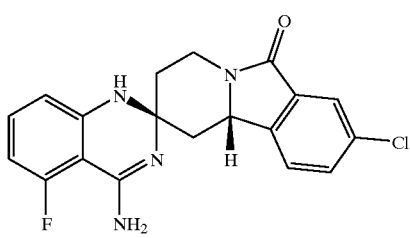

Obtained as the trifluoroacetate salt (amorphous) after purification by reverse-phase HPLC. MS (+CI) $^m$/z 371 [M+H]$^+$; MS (–CI) $^m$/z 369 [M–H]$^+$.

The compounds of Examples 11 and 12 were obtained from 2-amino-6-fluorobenzamidine dihydrochloride and 9-chloro-1,3,4,10b-tetrahydropyrido[2,1-a]isoindole-2,6-dione (Preparation 15).

EXAMPLES 11

(±)-(R*R*)-4'-Amino-9-chloro-5'-fluoro-1,3,4,10b-tetrahydrospiro[pyrido[2,1-a]isoindole-2,2'(1'H)-quinazoline]-6-one

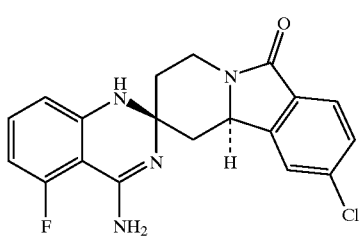

Obtained as the hydrochloride salt, m.p. 225° C. (dec).

EXAMPLE 12

(±)-(R*S*)-4'-Amino-9-chloro-5'-fluoro-1,3,4,10b-tetrahydrospiro[pyrido[2,1-a]isoindole-2,2'(1'H)-quinazoline]-6-one

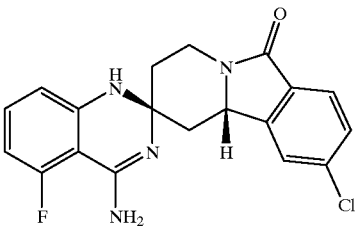

Obtained as the hydrochloride salt, m.p. 210° C. (dec).

The compounds of Examples 13 and 14 were obtained from 2-amino-6-fluorobenzamidine dihydrochloride and 10-chloro-1,3,4,10b-tetrahydropyrido[2,1-a]isoindole-2,6-dione (Preparation 14).

EXAMPLE 13

(±)-(R*R*)-4'-Amino-10-chloro-5'-fluoro-1,3,4,10b-tetrahydrospiro[pyrido[2,1-a]isoindole-2,2'(1'H)-quinazoline]-6-one

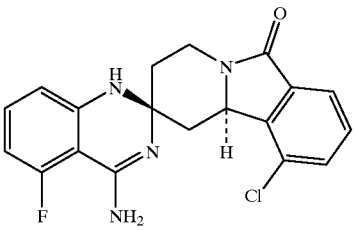

Obtained as the hydrochloride salt. MS (+CI) $^m$/z 371 [M+H]$^+$.

EXAMPLE 14

(±)-(R*S*)-4'-Amino-10-chloro-5'-fluoro-1,3,4,10b-tetrahydrospiro[pyrido[2,1-a]isoindole-2,2'(1'H)-quinazoline]-6-one

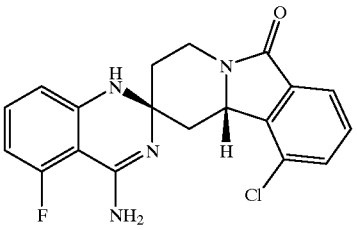

Obtained as the hydrochloride salt. MS (+CI) $^m$/z 371 [M+H]$^+$.

The compounds of Examples 15 and 16 were prepared from 2-amino-6-fluorobenzamidine dihydrochloride and 7,8-dichloro-1,3,4,10b-tetrahydropyrido[2,1-a]isoindole-2,6-dione (Preparation 5).

EXAMPLE 15

(±)-(R*R*)-4'-Amino-7,8-dichloro-5'-fluoro-1,3,4,10b-tetrahydrospiro[pyrido[2,1-a]isoindole-2,2'(1'H)-quinazoline]-6-one

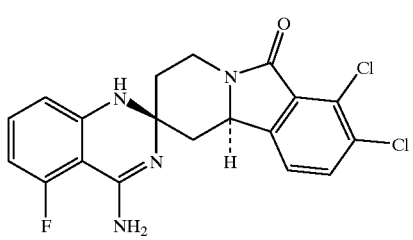

Obtained as the hydrochloride salt, m.p. 258–260° C.

EXAMPLE 16

(±)-(R*S*)-4'-Amino-7,8-dichloro-5'-fluoro-1,3,4,10b-tetrahydrospiro[pyrido[2,1-a]isoindole-2,2'(1'H)-quinazoline]-6-one

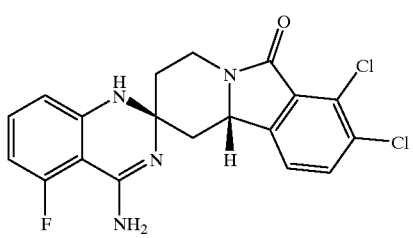

Obtained as the hydrochloride salt, m.p. 259–261° C.

The compounds of Examples 17 and 18 were obtained from 2-amino-6-fluorobenzamidine dihydrochloride and 7-methyl-1,3,4,10b-tetrahydropyrido[2,1-a]isoindole-2,6-dione (Preparation 11).

EXAMPLE 17

(±)-(R*R*)-4'-Amino-7-methyl-5'-fluoro-1,3,4,10b-tetrahydrospiro[pyrido[2,1-a]isoindole-2,2'(1'H)-quinazoline]-6-one

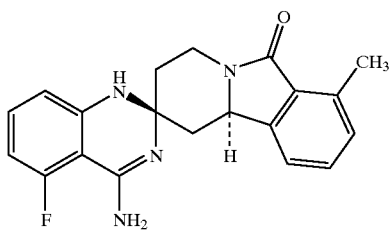

Obtained as the hydrochloride salt, m.p. 201–204° C.

EXAMPLE 18

(±)-(R*S*)-4'-Amino-7-methyl-5'-fluoro-1,3,4,10b-tetrahydrospiro[pyrido[2,1-a]isoindole-2,2'(1'H)-quinazoline]-6-one

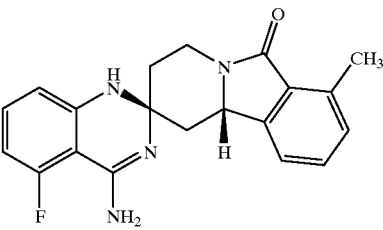

Obtained as the hydrochloride salt, m.p. 215–218° C.

The compounds of Examples 19 and 20 were obtained from 2-amino-6-fluorobenzamidine dihydrochloride and 8-methyl-1,3,4,10b-tetrahydropyrido[2,1-a]isoindole-2,6-dione (Preparation 8).

EXAMPLE 19

(±)-(R*R*)-4'-Amino-8-methyl-5'-fluoro-1,3,4,10b-tetrahydrospiro[pyrido[2,1-a]isoindole-2,2'(1'H)-quinazoline]-6-one

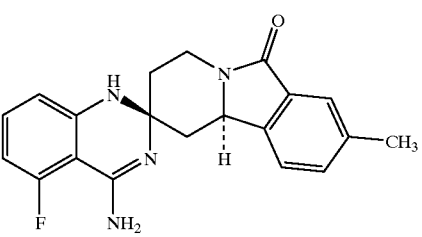

Obtained as the hydrochloride salt, m.p. 238–239° C.

EXAMPLE 20

(±)-(R*S*)-4'-Amino-8-methyl-5'-fluoro-1,3,4,10b-tetrahydrospiro[pyrido[2,1-a]isoindole-2,2'(1'H)-quinazoline]-6-one

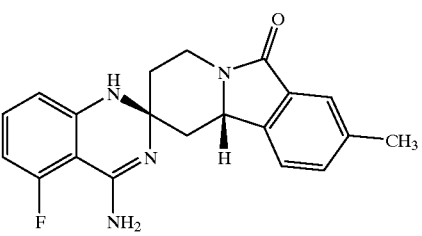

Obtained as the hydrochloride salt, m.p. 222–224° C.

The compounds of Examples 21 and 22 were prepared from 2-amino-6-fluorobenzamidine dihydrochloride and 8-methoxy-1,3,4,10b-tetrahydropyrido[2,1-a]isoindole-2,6-dione (Preparation 13).

EXAMPLE 21

(±)-(R*R*)-4'-Amino-8-methoxy-5'-fluoro-1,3,4,10b-tetrahydrospiro[pyrido[2,1-a]isoindole-2,2'(1'H)-quinazoline]-6-one

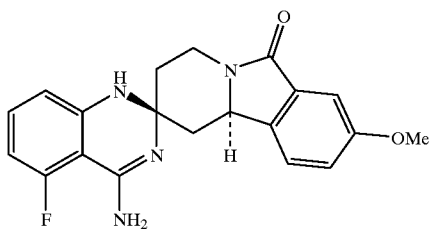

Obtained as the hydrochloride salt. MS (+CI) $^m$/z 367 [M+H]$^+$.

EXAMPLE 22

(±)-(R*S*)-4'-Amino-8-methoxy-5'-fluoro-1,3,4,10b-tetrahydrospiro[pyrido[2,1-a]isoindole-2,2'(1'H)-quinazoline]-6-one

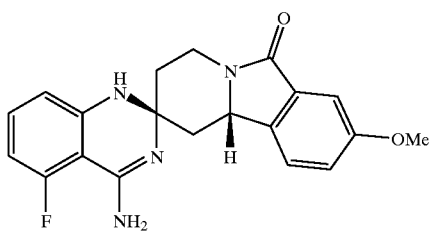

Obtained as the hydrochloride salt. MS (+CI) $^m$/z 367 [M+H]$^+$.

The compounds of Examples 23 and 24 were obtained from 2-amino-6-fluorobenzamidine dihydrochloride and 8-cyano-1,3,4,10b-tetrahydropyrido[2,1-a] isoindole-2,6-dione (Preparation 9).

EXAMPLE 23

(±)-(R*R*)-4'-Amino-8-cyano-5'-fluoro-1,3,4,10b-tetrahydrospiro[pyrido[2,1-a]isoindole-2,2'(1'H)-quinazoline]-6-one

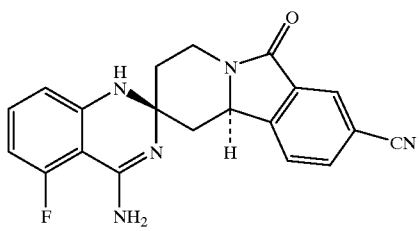

Obtained as the hydrochloride salt, m.p. 241° C. (dec).

EXAMPLE 24

(±)-(R*S*)-4'-Amino-8-cyano-5'-fluoro-1,3,4,10b-tetrahydrospiro[pyrido[2,1-a]isoindole-2,2'(1'H)-quinazoline]-6-one

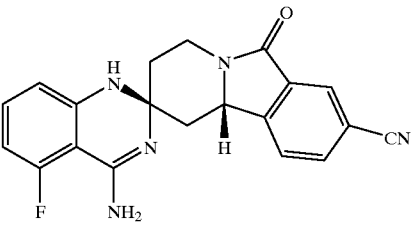

Obtained as the hydrochloride salt, m.p. 290° C. (dec).

The compounds of Examples 25 and 26 were obtained from from 2-amino-3,6-difluoro benzamidine hydrochloride and 8-cyano-1,3,4,10b-tetrahydropyrido[2,1-a]isoindole-2,6-dione (Preparation 9).

EXAMPLE 25

(±)-(R*R*)-4'-Amino-8-cyano-5',8'-difluoro-1,3,4,10b-tetrahydrospiro[pyrido[2,1-a]isoindole-2,2'(1'H)-quinazoline]-6-one

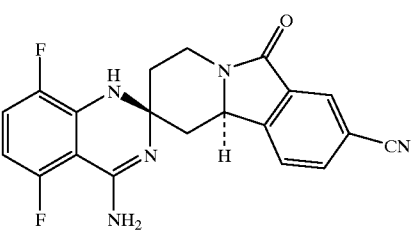

Obtained as the hydrochloride salt, m.p. 243° C. (dec).

EXAMPLE 26

(±)-(R*S*)-4'-Amino-8-cyano-5',8'-difluoro-1,3,4,10b-tetrahydrospiro[pyrido[2,1-a]isoindole-2,2'(1'H)-quinazoline]-6-one

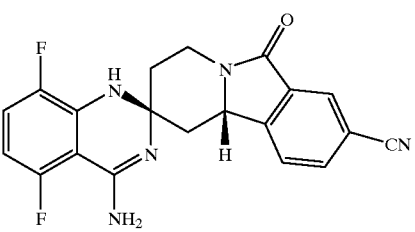

M.p. 180° C. (dec).

The compounds of Examples 27 and 28 were obtained from 2-amino-6-fluorobenzamidine dihydrochloride and 7,8,10,10a-tetrahydropyrido[3,4-a]indolizine-5,9-dione (Preparation 10).

EXAMPLE 27

(±)-(R*R*)-4'-Amino-5'-fluoro-7,8,10,10a-tetrahydrospiro[pyrido[3,4-a]indolizine-9,2'(1'H)-quinazoline]-5-one

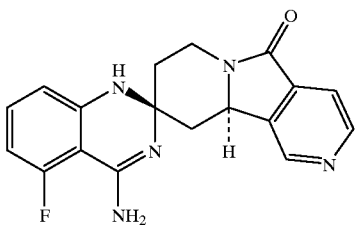

Obtained as the hydrochloride salt. MS (+CI) $^m/z$ 338 [M+H]$^+$; 300 MHz $^1$H NMR (d$_6$-DMSO) 8.97 (1H, s), 8.72 (1H, d, J 5.1 Hz), 7.67 (1H, d, J 5 Hz), 7.20 (1H, q, J 7 Hz), 6.8 (1H, br.s), 6.46–6.38 (2H, m), 4.97 (1H, dd, J 3.6, 12 Hz), 4.18 (1H, dd, J 4.5 12.6 Hz), 3.45 (1H, dt, 3.3, 12.9 Hz), 2.76–2.72 (1H, m), 1.97 (1H, d, J 12 Hz), 1.45 (1H, dt, J 5.4, 12.9 Hz), 1.10 (1H, t, J 12.0 Hz).

EXAMPLE 28

(±)-(R*S*)-4'-Amino-5'-fluoro-7,8,10,10a-tetrahydrospiro[pyrido[3,4-a]indolizine-9,2'(1'H)-quinazoline]-5-one

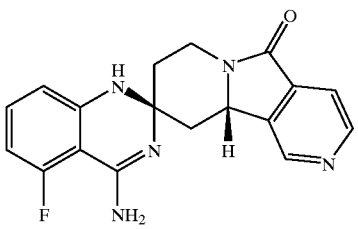

MS (+CI) $^m/z$ 338 [M+H]$^+$; 300 MHz $^1$H NMR (d$_6$-DMSO) 8.95 (1H, s), 8.74 (1H, d, J 4.8 Hz), 7.69 (1H, d, J 5.1 Hz), 7.44–7.25 (3H, m), 6.78 (1H, d, J 7.5 Hz), 6.52–6.46 (1H, m), 4.94 (1H, dd, J 3.6, 12.3 Hz), 4.20 (1H, dd, J 4.8, 13.8 Hz), 3.8–3.43 (1H, dd, obscured by H$_2$O), 2.71 (1H, br.d, J 9Hz), 1.98 (1H, d, J 13.2 Hz), 1.55 (1H, dt, J 5.1, 12.9 Hz), 1.26 (1H, t, J 12.9 Hz).

The compounds of Examples 29 and 30 were obtained from 2-amino-6-fluorobenzamidine dihydrochloride and 6b,7,9,10-tetrahydronaphtho[2,1-a]indolizine-8,12-dione (Preparation 12).

EXAMPLE 29

(±)-(R*R*)-4'-Amino-5'-fluoro-6b,7,9,10-tetrahydrospiro[naphtho[2,1-a]indolizine-8,2'(1'H)-quinazoline]-12-one

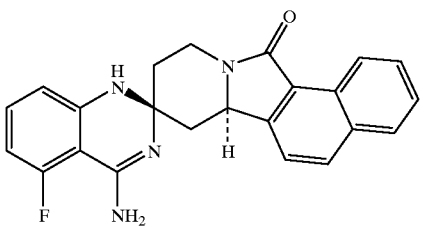

Obtained as the hydrochloride salt, m.p. 208–210° C.

EXAMPLE 30

(±)-(R*S*)-4'-Amino-5'-fluoro-6b,7,9,10-tetrahydrospiro[naphtho[2,1-a]indolizine-8,2'(1'H)-quinazoline]-12-one

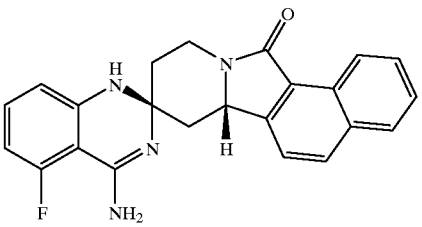

Obtained as the hydrochloride salt, m.p. 235–237° C.

SCREENS

The pharmacological activity of compounds according to the invention was tested in the following screens.

Screen 1

The activity of compounds of formula (I), or a pharmaceutically acceptable salt, enantiomer or tautomer thereof, may be screened for nitric oxide synthetase inhibiting activity by a procedure based on that of Förstermann et al., Eur. J. Pharm., 1992, 225, 161–165. Nitric oxide synthase converts $^3$H-l-arginine into $^3$H-l-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM l-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% CO$_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 μl of substrate cocktail (50 mM Tris-HCl (pH 7.5 at 20° C.), 400 μM NADPH, 20 μM flavin adenine dinucleotide, 20 μM flavin mononucleotide, 4 μM tetrahydrobiopterin, 12 μM l-arginine and 0.025 mCi l-[$^3$H] arginine) is added to wells of a 96 well filter plate (0.45 μM pore size) containing 25 μl of a solution of test compound in 50 mM Tris-HCl. The reaction is started by adding 50 μl of cell lysate (prepared as above) and after incubation for 1 hour at room temperature is terminated by addition of 50 μl of an aqueous solution of 3 mM nitroarginine and 21 mM EDTA.

Labelled l-citrulline is separated from labelled l-arginine using Dowex AG-50W. 150 μl of a 25% aqueous slurry of Dowex 50W (Na$^+$ form) is added to the assay after which the whole is filtered into 96 well plates. 75 μl of filtrate is sampled and added to wells of 96 well plates containing solid scintillant. After allowing the samples to dry the l-citrulline is quantified by scintillation counting.

In a typical experiment basal activity is 300 dpm per 75 μl sample which is increased to 1900 dpm in the reagent controls. Compound activity is expressed as $IC_{50}$ (the concentration of drug substance which gives 50% enzyme inhibition in the assay) and aminoguanidine, which gives an $IC_{50}$ (50% inhibitory concentration) of 10 μM, is tested as a standard to verify the procedure. Compounds are tested at a range of concentrations and from the inhibitions obtained $IC_{50}$ values are calculated. Compounds that inhibit the enzyme by at least 25% at 100 μM are classed as being active and are subjected to at least one retest.

In the above screen, the compounds of Examples 1 to 30 were tested and gave $IC_{50}$ values of less than 25 μM indicating that they are expected to show useful therapeutic activity.

Screen 2

Compounds also show activity against the human form of induced nitric oxide synthase as can be demonstrated in the following assay.

Enzyme is prepared, after induction, from the cultured human colon adrenocarcinoma cell line DLD1 (obtained from the European Collection of Animal Cell Culture—cell line number 90102540). DLD1 cells are cultured in RPMI 1640 medium supplemented with 10% foetal bovine serum, 4 mM l-glutamine and antibiotics (100 units/ml penicillin G, 100 μg/ml streptomycin and 0.25 μg/ml amphotericin B). Cells are routinely grown in 225 cm³ flasks containing 35 ml medium kept at 37° C. and in a humidified atmosphere containing 5% $CO_2$.

Nitric oxide synthase is produced by cells in response to interferon-γ (IFN-γ) and interleukin-1β (IL-1β). The medium from confluent flasks is removed and replaced with 25 ml (per flask) of fresh medium containing 250 units/ml IL-1β and 1000 units/ml IFN-γ. After a period of 17–20 hours in culture, harvesting of cells is accomplished by scraping the cell monolayer from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X100, 0.1 mM dithiothreitol and a cocktail of protease inhibitors including leupeptin (2 μg/ml), soya bean trypsin inhibitor (10 μg/ml), aprotonin (5 μg/ml) and phenylmethylsulphonyl fluoride (50 μg/ml).

For the assay, 25 μl of substrate cocktail (50 mM Tris-HCl (pH 7.5), 400 μM NADPH, 20 μM flavin adenine dinucleotide, 20 μM flavin mononucleotide and 4 μM tetrahydrobiopterin) is added to the wells of a 96-well plate. Test compounds are preincubated with enzyme by adding together with 40 μl of cell lysate (prepared as above) and incubating for 1 hour at 37° C. at the end of which period 10 μl of 30 μM l-arginine and 0.025 μCi of l-[³H]-arginine in 50 mM Tris-HCl is added to start the enzymatic reaction. Incubation is continued for a further 1 hour at 37° C. The reaction is terminated by addition of 50 μl of an aqueous solution of 3 mM nitroarginine and 21 mM EDTA.

Labelled l-citrulline is separated from labelled l-arginine using Dowex AG-50W. 120 μl of a 25% aqueous slurry of Dowex 50W is added to 96 well filter plates (0.45 μm pore size). To this is added 120 μl of terminated assay mix. 75 μl of filtrate is sampled and added to the wells of 96 well plates containing solid scintillant. After allowing the samples to dry the l-citrulline is quantified by scintillation counting.

In a typical experiment basal activity is 300 dpm per 75 μl sample of reagent controls, which is increased to 3000 dpm in the presence of enzyme. Compound activity is expressed as $IC_{50}$ (the concentration of drug substance which gives 50% enzyme inhibition in the assay) and l-NMMA, which gives an $IC_{50}$ of about 0.4 μM is tested as a standard to verify the procedure. Compounds are tested at a range of concentrations and from the inhibitions obtained $IC_{50}$ values are calculated.

In this screen the compounds of Examples 1 to 30 give $IC_{50}$ values less than 25 μM, indicating that they are predicted to show useful therapeutic activity.

What is claimed is:

1. A compound of formula (I)

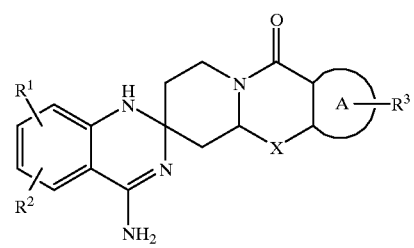

(I)

wherein $R^1$ and $R^2$ independently represent hydrogen, C1 to 6 alkyl, C2 to 6 alkenyl, C2 to 6 alkynyl, C1 to 6 alkoxy, C1 to 6 alkylthio, halogen, hydroxy, trifluoromethyl or amino;

$R^3$ represents one or more substituents independently selected from hydrogen, C1 to 6 alkyl, C2 to 6 alkenyl, C2 to 6 alkynyl, C1 to 6 alkoxy, C1 to 6 alkylthio, halogen, hydroxy, trifluoromethyl, amino, cyano, nitro, trifluoromethoxy, methanesulphonyl, sulphamoyl, —$NR^4R^5$, —$COOR^6$, —$CONR^7R^8$, benzyloxy, phenyl, or a 5-membered heterocyclic aromatic ring containing 1 to 3 heteroatoms which may be the same or different and are selected from O, N and S, which phenyl or 5-membered heterocyclic aromatic ring is optionally substituted, the optionally substituents being C1 to 6 alkyl, halogen, cyano, nitro, hydroxy, C1 to 6 alkoxy, trifluoromethyl and trifluoromethoxy;

$R^4$, $R^5$ and $R^6$ independently represent hydrogen or C1 to 6 alkyl;

$R^7$ and $R^8$ independently represent hydrogen, C1 to 6 alkyl or phenyl, which phenyl is optionally substituted by one or more groups independently selected from C1 to 6 alkyl, halogen, cyano, nitro, hydroxy, C1 to 6 alkoxy, trifluoromethyl and trifluoromethoxy;

X represents —$(CH_2)_n$—, wherein n represents zero or 1; and

A represents a benzo or naphtho ring system;

or a pharmaceutically acceptable salt, enantiomer, racemate or tautomer thereof.

2. A compound of formula (I), according to claim 1, wherein A represents a benzo ring.

3. A compound of formula (I), according to claim 1, wherein $R^1$ represents hydrogen.

4. A compound of formula (I), according to claim 1, wherein $R^1$ represents fluoro.

5. A compound of formula (I), according to claim 1, wherein $R^2$ represents fluoro.

6. A compound of formula (I), according to claim 1, wherein X represents —$(CH_2)_n$— and n represents zero.

7. A compound of formula (I) according to claim 1 which is:

(R*R*)-4'-amino-5'-fluoro-1,3,4,10a-tetrahydrospiro[pyrido[2,1-a]isoindole-2,2'(1'H)quinazoline]-6-one;
(R*S*)-4'-amino-5'-fluoro-1,3,4,10a-tetrahydrospiro[pyrido[2,1-a]isoindole-2,2'(1'H)quinazoline]-6-one;
(R*R*)-4'-amino-7-chloro-5'-fluoro-1,3,4,10b-tetrahydrospiro[pyrido[2,1-a]isoindole-2,2'(1'H)-quinazoline]-6-one;
(R*S*)-4'-amino-7-chloro-5'-fluoro-1,3,4,10b-tetrahydrospiro[pyrido[2,1-a]isoindole-2,2'(1'H)-quinazoline]-6-one;
(R*R*)-4'-amino-8-chloro-5'-fluoro-1,3,4,10b-tetrahydrospiro[pyrido[2,1-a]isoindole-2,2'(1'H)-quinazoline]-6-one;
(R*S*)-4'-amino-8-chloro-5'-fluoro-1,3,4,10b-tetrahydrospiro[pyrido[2,1-a]isoindole-2,2'(1'H)-quinazoline]-6-one;
(R*R*)-4'-amino-9-chloro-5'-fluoro-1,3,4,10b-tetrahydrospiro[pyrido[2,1-a]isoindole-2,2'(1'H)-quinazoline]-6-one;
(R*S*)-4'-amino-9-chloro-5'-fluoro-1,3,4,10b-tetrahydrospiro[pyrido[2,1-a]isoindole-2,2'(1'H)-quinazoline]-6-one;
(R*R*)-4'-amino-10-chloro-5'-fluoro-1,3,4,10b-tetrahydrospiro[pyrido[2,1-a]isoindole-2,2'(1'H)-quinazoline]-6-one;
(R*S*)-4'-amino-10-chloro-5'-fluoro-1,3,4,10b-tetrahydrospiro[pyrido[2,1-a]isoindole-2,2'(1'H)-quinazoline]-6-one;
(R*R*)-4'-amino-7,8-dichloro-5'-fluoro-1,3,4,10b-tetrahydrospiro[pyrido[2,1-a]isoindole-2,2'(1'H)-quinazoline]-6-one;
(R*S*)-4'-amino-7,8-dichloro-5'-fluoro-1,3,4,10b-tetrahydrospiro[pyrido[2,1-a]isoindole-2,2'(1'H)-quinazoline]-6-one;
(R*R*)-4'-amino-7-methyl-5'-fluoro-1,3,4,10b-tetrahydrospiro[pyrido[2,1-a]isoindole-2,2'(1'H)-quinazoline]-6-one;
(R*S*)-4'-amino-7-methyl-5'-fluoro-1,3,4,10b-tetrahydrospiro[pyrido[2,1-a]isoindole-2,2'(1'H)-quinazoline]-6-one;
(R*R*)-4'-amino-8-methyl-5'-fluoro-1,3,4,10b-tetrahydrospiro[pyrido[2,1-a]isoindole-2,2'(1'H)-quinazoline]-6-one;
(R*S*)-4'-amino-8-methyl-5'-fluoro-1,3,4,10b-tetrahydrospiro[pyrido[2,1-a]isoindole-2,2'(1'H)-quinazoline]-6-one;
(R*R*)-4'-amino-8-methoxy-5'-fluoro-1,3,4,10b-tetrahydrospiro[pyrido[2,1-a]isoindole-2,2'(1'H)-quinazoline]-6-one;
(R*S*)-4'-amino-8-methoxy-5'-fluoro-1,3,4,10b-tetrahydrospiro[pyrido[2,1-a]isoindole-2,2'(1'H)-quinazoline]-6-one;
(R*R*)-4'-amino-8-cyano-5'-fluoro-1,3,4,10b-tetrahydrospiro[pyrido[2,1-a]isoindole-2,2'(1'H)-quinazoline]-6-one;
(R*S*)-4'-amino-8-cyano-5'-fluoro-1,3,4,10b-tetrahydrospiro[pyrido[2,1-a]isoindole-2,2'(1'H)-quinazoline]-6-one;
(R*R*)-4'-amino-8-cyano-5',8'-difluoro-1,3,4,10b-tetrahydrospiro[pyrido[2,1-a]isoindole-2,2'(1'H)-quinazoline]-6-one;
(R*S*)-4'-amino-8-cyano-5',8'-difluoro-1,3,4,10b-tetrahydrospiro[pyrido[2,1-a]isoindole-2,2'(1'H)-quinazoline]-6-one;
(R*R*)-4'-amino-5'-fluoro-6b,7,9,10-tetrahydrospiro[naphtho[2,1-a]indolizine-8,2'(1'H)-quinazoline]-12-one;
(R*S*)-4'-amino-5'-fluoro-6b,7,9,10-tetrahydrospiro[naphtho[2,1-a]indolizine-8,2'(1'H)-quinazoline]-12-one;
or a pharmaceutically acceptable salt, enantiomer or tautomer thereof.

8. A pharmaceutical composition comprising a compound of formula (I) according to claim 1, or a pharmaceutically acceptable salt, enantiomer or tautomer thereof, in admixture with a pharmaceutically acceptable adjuvant, diluent or carrier.

9. A method of treating, or reducing the risk of human diseases or conditions in which inhibition of nitric oxide synthase activity ial which comprises administering a therapeutically effective amount of a compound of formula (I), as defined in claim 1, or a pharmaceutically acceptable salt, enantiomer or tautomer thereof, to a person suffering from, or at increased risk of, such diseases or conditions.

10. A method of treatment according to claim 9 in which it is predominantly inducible nitric oxide synthase that is inhibited.

11. A method of treating, or reducing the risk of, inflammatory disease in a person suffering from, or at risk of, said disease, wherein the method comprises administering to the person a therapeutically effective amount of a compound of formula (I), as defined in claim 1, or a pharmaceutically acceptable salt, enantiomer or tautomer thereof.

12. The method of treatment as claimed in claim 11 wherein the disease is asthma or rheumatoid arthritis.

13. A method of treating, or reducing the risk of, pain in a person suffering from, or at risk of, said condition, wherein the method comprises administering to the person a therapeutically effective amount of a compound of formula (I), as defined in claim 1, or a pharmaceutically acceptable salt, enantiomer or tautomer thereof.

14. A process for the preparation of a compound of formula (I), as defined in claim 1, or a pharmaceutically acceptable salt, enantiomer or tautomer thereof, wherein the process comprises reaction of a compound of formula (II), or a salt thereof:

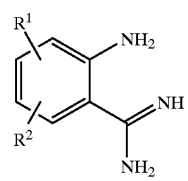

(II)

wherein $R^1$ and $R^2$ are as defined in claim 1, with a compound of formula (III) or a protected derivative thereof:

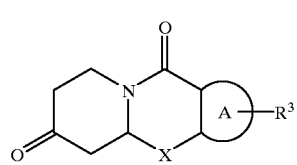

(III)

wherein $R^3$, A and X are as defined in claim 1.

* * * * *